United States Patent [19]

Nabai et al.

[11] Patent Number: 5,325,857
[45] Date of Patent: Jul. 5, 1994

[54] SKIN BIOPSY DEVICE AND METHOD

[76] Inventors: Hossein Nabai, 14555 Levan Rd., Ste. 410, Livonia, Mich. 48154; Homayoon Rahbari, 1314 N. Macomb St., P.O. Box 360, Monroe, Mich. 48161

[21] Appl. No.: 88,678

[22] Filed: Jul. 9, 1993

[51] Int. Cl.⁵ .............................................. A61B 10/00
[52] U.S. Cl. ................................................... 128/754
[58] Field of Search .................. 128/749, 751–754; 606/167, 170

[56] References Cited

U.S. PATENT DOCUMENTS

| | | |
|---|---|---|
| 363,538 | 5/1918 | Penny . |
| 3,566,871 | 3/1971 | Richter et al. . |
| 4,409,206 | 10/1983 | Stricker . |
| 4,605,005 | 8/1986 | Sheehan . |
| 4,817,631 | 4/1989 | Schrepp-Pesch et al. ........... 128/753 |
| 4,850,373 | 7/1989 | Zatkoekal et al. .................. 128/749 |

FOREIGN PATENT DOCUMENTS 2609624  7/1988  France ................. 128/749

*Primary Examiner*—Max Hindenburg
*Attorney, Agent, or Firm*—Alex Rhodes

[57] ABSTRACT

A device and method for performing a routine skin biopsy. In the first aspect of the invention, the device is comprised of a syringe, a detachable needle mounted on one end portion of the syringe, a biopsy punch attached to the same end portion which is accessible only when the needle is removed from the syringe, and a small pad of an absorbable sponge. The needle is removed from the syringe after a patient has been anesthetized with the syringe to expose the biopsy punch. A biopsy specimen is excised with the punch. Thereafter, a cylindrical plug is cut from the pad of absorbable sponge with the biopsy punch and implanted into the biopsy site. In a second aspect of the invention, a small cylindrical sponge is stored in the center of the biopsy punch and is implanted into the biopsy site with the syringe after a specimen has been excised with the punch.

12 Claims, 3 Drawing Sheets

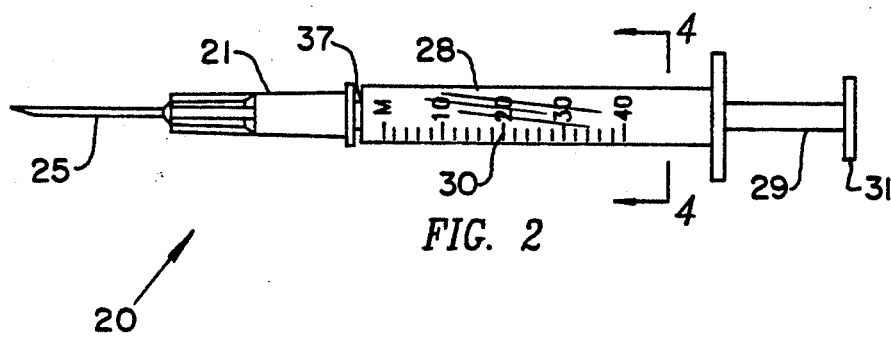
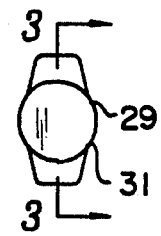
FIG. 2
FIG. 1
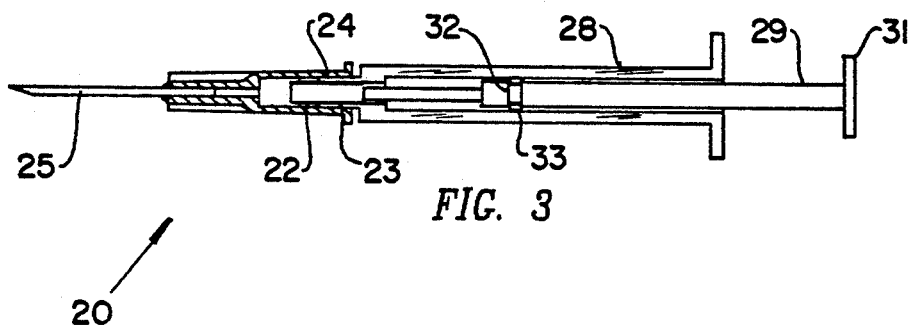
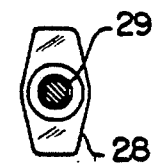
FIG. 3
FIG. 4
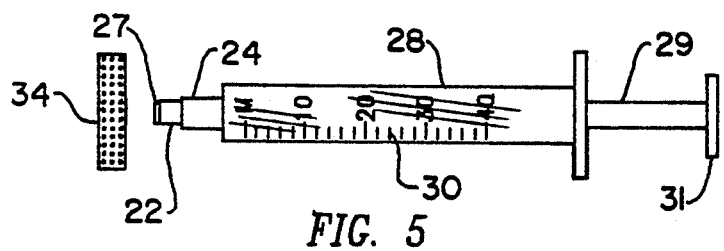
FIG. 5
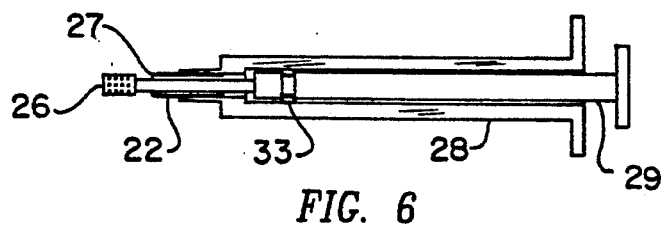
FIG. 6

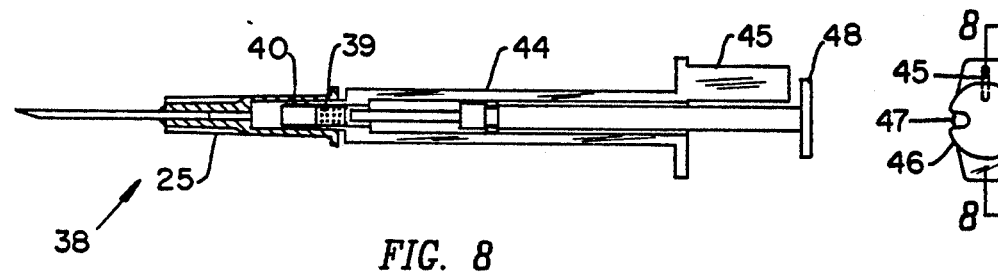
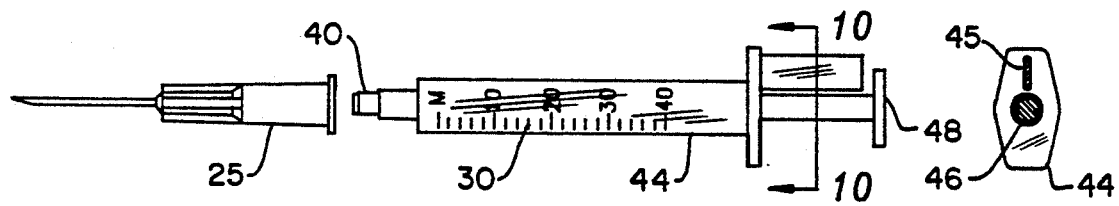
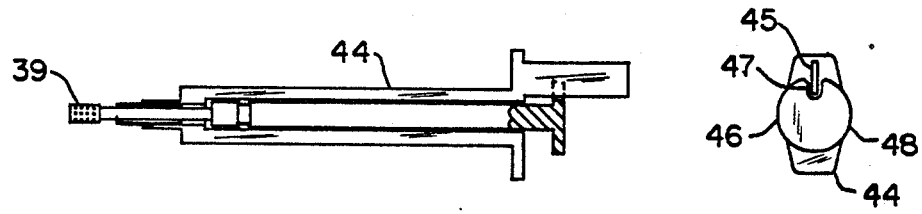
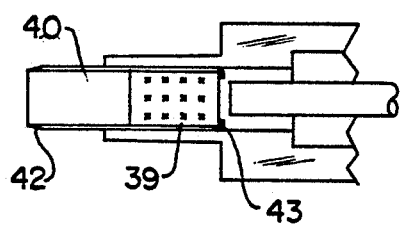
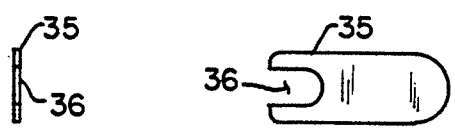
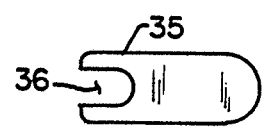

SKIN BIOPSY DEVICE AND METHOD

FIELD OF THE INVENTION

This invention relates to surgical devices and more particularly to a disposable device for performing skin biopsies.

BACKGROUND OF THE INVENTION

A skin biopsy is a well known medical procedure for diagnosing skin disorders. The usual procedure is to anesthetize the biopsy site, excise a small cylindrical specimen for analysis at a pathology laboratory and to repair the biopsy site with sutures or butterfly bandages.

The disadvantages with the usual procedure is that it requires the use of several medical devices, requires hemostasis and repair of the biopsy site, is time consuming, exposes medical personnel to infection, and sometimes damages the biopsy specimen because of excessive handling. Another disadvantage is that there is a likelihood of inducing excessive scar tissue at the biopsy site with sutures or butterfly bandages. Another disadvantage is that some patients suffer anxiety during suturing of wounds.

In our co-pending U.S. application Ser. No. 08/056,399, a device and method were disclosed for performing a skin biopsy using an open cell surgical sponge for controlling bleeding and repairing the biopsy site. The present invention is a further development in our device and method.

SUMMARY OF THE INVENTION

The present invention is an efficient, disposable device for performing skin biopsies. The device is comprised of a syringe, a small circular punch attached to one end of the syringe, a detachable needle attached to the same end of the syringe and a small pad of an open cell absorbable sponge. The punch is exposed when the needle is removed from the end of the syringe.

One feature of the invention is that the syringe's plunger is used for extracting a specimen and the surgical sponge from the biopsy punch. Another feature of the invention is that an aid is provided for removing the needle from the syringe.

In a first aspect of the invention, after a biopsy specimen is excised from a patient with the punch, a small surgical sponge of the same diameter as the specimen is cut from a larger sponge with the biopsy punch and implanted into the biopsy site with the syringe.

In a second aspect of the invention, after the biopsy specimen is excised, a small pre-cut open cell surgical sponge stored in the punch is implanted into the biopsy site with the syringe. One feature of the second aspect is that an anesthetic is drawn through the sponge when the anesthetic is drawn into the syringe.

Further features and benefits of our invention, will be apparent from the ensuing detailed description taken in conjunction with the accompanying drawings. The best mode which is contemplated in practicing our invention is disclosed and the subject matter in which exclusive property rights are claimed is set forth in each of the numbered claims which are appended to the detailed description.

BRIEF DESCRIPTION OF THE DRAWINGS

FIG. 1 is an end view of a biopsy device according to the present invention.

FIG. 2 is a front view of the biopsy device.

FIG. 3 is a cross-sectional view taken on the line 3—3 in FIG. 1.

FIG. 4 is a cross-sectional view taken on the line 4—4 in FIG. 2.

FIG. 5 is a front view showing the detachable needle removed from the syringe biopsy device and a small pad of an open cell surgical sponge.

FIG. 6 is a cross-sectional view of the syringe taken in the same manner as FIG. 3 with the plunger of the syringe depressed to extract a portion of the surgical sponge from the end of the syringe.

FIG. 7 is an end view of an alternate embodiment.

FIG. 8 is a cross-sectional view taken on the line 8—8 in FIG. 7.

FIG. 9 is a front view of the alternate embodiment showing the needle removed from the syringe.

FIG. 10 is a cross-sectional view taken on the line 10—10 in FIG. 9.

FIG. 11 is a cross-sectional view of the syringe taken in the same manner as FIG. 8 with the plunger of the syringe depressed to extract a surgical sponge from the syringe.

FIG. 12 is an end view of the alternate embodiment with the plunger of the syringe rotated clockwise 90 degrees.

FIG. 13 is a front view of a tool for removing the needle from the syringe.

FIG. 14 is an end view of the tool.

FIG. 15 is an enlarged fragmentary portion of FIG. 8.

DETAILED DESCRIPTION OF THE PREFERRED EMBODIMENT

Figure 16:
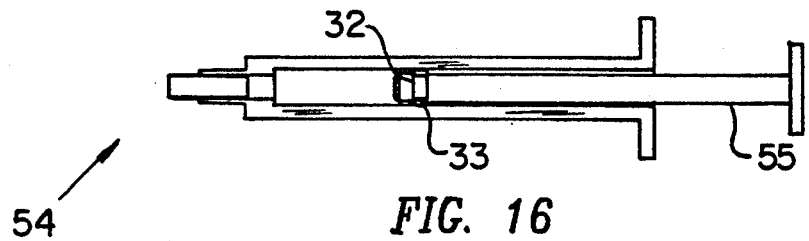
FIG. 16 is a longitudinal cross-sectional view of an alternate embodiment.
Figure 17:
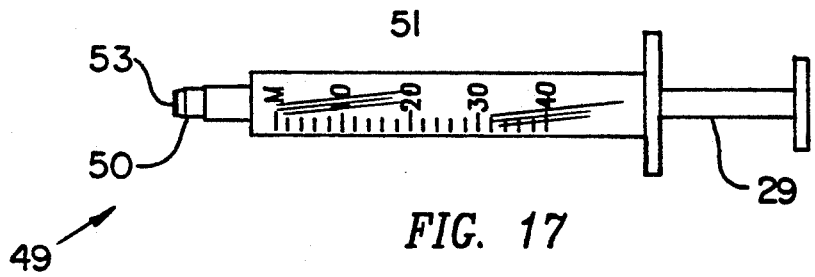
FIG. 17 is a front view of an alternate embodiment.
Figure 18:
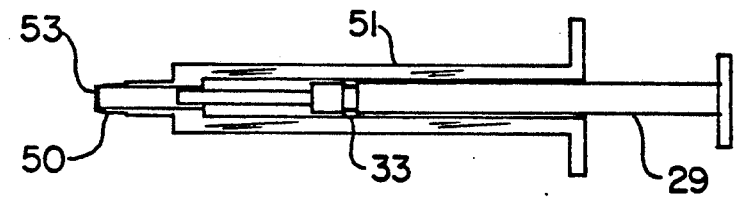
FIG. 18 is a longitudinal cross-sectional view of the alternate embodiment of FIG. 17.
Figure 19:
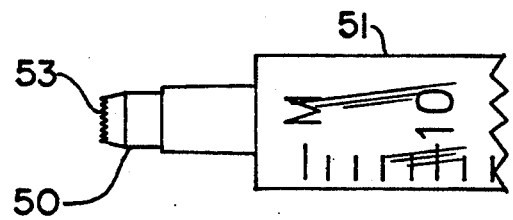
FIG. 19 is an enlarged fragmentary portion of FIG. 17.
Figure 20:
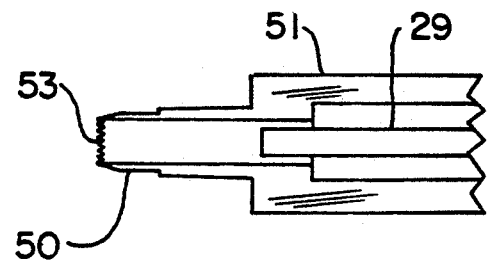
FIG. 20 is an enlarged fragmentary portion of FIG. 18.

Referring now to the drawings wherein like numerals designate like and corresponding parts throughout the several views, a disposable device 20 for performing a skin biopsy is shown in FIGS. 1 through 6, inclusive, according to the invention.

The biopsy device comprises a syringe 21, a thin sharp cylindrical punch 22 pressed into an aperture 23 of a cylindrical end portion 24 of the syringe 21, a detachable needle 25 attached to the outside of same end portion 24 and an absorbable surgical sponge 26. The punch 22 is exposed when the needle 25 is removed from the syringe 21.

The punch 22 is a thin cylindrical blade with a sharp end portion 27. In FIGS. 17 through 20, an embodiment 49 is shown wherein a punch 50 is shown as formed from the same piece as a body 51 of a syringe 52 and having sharp serrations 53 at the end of the punch 50.

The construction of the syringe 21 is best seen in FIGS. 3 and 6. The syringe 21 has a transparent plastic body 28 and a cylindrical plunger 29 which is slideably mounted in the body 28. The exterior of the body 28 has graduations 30 for measuring the amount of a local anesthetic in the syringe 21.

At one end of the plunger 29 there is a knob 31 for sliding the plunger 29 in and out of the body 28. At the other end of the plunger 29 the diameter is reduced for extracting a biopsy specimen (not shown) and the surgical sponge 26 from the punch 22. At an intermediate position on the plunger 29 there is a groove 32 which receives an O-ring 33 for sealing the plunger 29 in the body 28.

In FIG. 16 an embodiment 54 is shown wherein the groove 32 and O-ring 33 are at the end portion of a plunger 55. The embodiment of 36 requires a forceps (not shown) for extracting the biopsy specimen and sponge from the punch 22.

With reference to FIG. 5, the sponge is cut from a rectangular pad 34 of a porous material which is absorbed completely by a patient with little tissue reaction. When the sponge 26 is implanted into a bleeding site, the sponge 26 absorbs blood, swells and terminates the flow of blood. By filling up the biopsy site, the sponge 26 promotes healing without the necessity of suturing.

One material which has been evaluated and found to be acceptable for our invention is an absorbable gelatin sponge manufactured by the Upjohn Company under the registered trademark "GELFOAM". It is a water-insoluble, off-white, non-elastic, porous, pliable product made from purified pork skin gelatin USP granules and is available in the form of pads.

The manner of using our invention is as follows. The syringe 21 is either pre-filled with a local anesthetic or filled in a conventional way by withdrawing the plunger 29 from the body 28 with the end of the needle 25 immersed in the anesthetic. The anesthetic is then administered through the needle 25 into a biopsy site. The needle 25 is removed with the flat bladed tool 35 shown in FIGS. 13 and 14 by engaging the notched portion 36 of the tool 35 with the end portion 37 of the syringe 21 and prying the needle 25 loose from the syringe 21. A small cylindrical specimen is excised from the patient by pressing the sharp end of the punch 22 against a patient's skin and rotating the body of the syringe 21.

After the specimen has been excised, the specimen is extracted from the punch 22 by sliding the plunger 29 into the syringe's body 28. The plunger 29 is then displaced a small distance in the body 28 to provide space for the surgical sponge 26. The punch 22 is pressed and rotated against a small pad of surgical sponge 26 to cut out a cylindrical portion of the pad 34 of about the same diameter as the cylindrical defect caused by removal of the specimen from the patient. The surgical sponge 26 is implanted into the biopsy site by sliding the plunger 29 into the body 28 to extract the cylindrical sponge 26 from the punch 22 and to implant the sponge 26 into the defect caused by the excising of the biopsy specimen.

In FIGS. 8–12 and 15, a second embodiment 38 is illustrated wherein a pre-cut surgical sponge 39 is stored in a biopsy punch 40. In this embodiment, the anesthetic passes through the pre-cut sponge 39 when the syringe 41 is filled and the anesthetic is administered to the patient.

With reference to FIG. 12, the sponge 39 is positioned a small distance apart from the knife edge portion 42 of the punch 40. The innermost end of the punch 40 has an inward facing flange portion 43 to prevent the sponge 39 from being drawn into the body 44 of the syringe 41 during the filling of the syringe 41 with the anesthetic. On the upper part of the body 44, there is a stop 45 which prevents ejection of the sponge 39 during the administration of the anesthetic.

When additional plunger travel is needed to extract a biopsy specimen from the punch 40 or to implant the sponge 39 into a biopsy site, additional travel is obtained, as shown in FIGS. 11 and 12, by rotating the plunger 46 ninety degrees to align the stop 45 with a groove 47 in the knob 48 of the body 44. One benefit of this embodiment 38 is a reduction in time for performing a biopsy. Another benefit is reduced likelihood of infection because handling is reduced.

The alternate embodiment 38 is used in a similar manner to the first embodiment, except that the plunger 46 is rotated ninety degrees to extract the specimen from the punch 40 and to implant the sponge 39 into the biopsy site.

From the foregoing it will be understood that our invention provides a device and method which reduces the time for performing a routine skin biopsy, reduces the likelihood of forming excessive scar tissue and protects medical personnel against infections.

Although several embodiments of our invention have been illustrated and described, it is not our intention to limit our invention to these embodiments since other embodiments can be provided by substitutions in materials and modifications in the shape, number and arrangements of parts and steps in our closure device and changes in steps in our method without departing from the spirit thereof.

We claim:

1. A device for performing a skin biopsy procedure comprising the combination of a syringe; a detachable needle mounted on the end of the syringe; and a thin cylindrical punch mounted on the same end of the syringe as said needle, said punch being only available for excising a specimen for analysis from a patient when said needle is removed from the end of said syringe.

2. The device for performing a skin biopsy procedure recited in claim 1 further comprising an open cell sponge for repairing a site from which said specimen has been excised.

3. The device for performing a skin biopsy procedure recited in claim 2 wherein said sponge is a formed cylindrical sponge stored in the interior of said punch.

4. The device for performing a skin biopsy procedure recited in claim 2 wherein said sponge is a porous and pliable product made from purified pork skin.

5. The device for performing a skin biopsy procedure recited in claim 1 further comprising a means for removing said needle from the end of said syringe.

6. A device for performing a skin biopsy procedure comprising: the combination of a syringe, said syringe having a transparent body, a plunger slideably mounted on said body, said plunger having one end portion which is adapted for extracting said specimen from a biopsy punch and a seal mounted at an intermediate position on said plunger; a detachable needle mounted on the end of the syringe; and a thin cylindrical biopsy punch fixed to the same end of the syringe as said needle, said punch being only available for excising a specimen for analysis from a patient when said needle is removed from the end of said syringe.

7. The device for performing a skin biopsy procedure recited in claim 6 wherein the punch is made from the same piece as said body.

8. The device for performing a skin biopsy procedure recited in claim 6 further comprising a plurality of sharp serrations at an end portion of said punch.

9. A method for performing a skin biopsy procedure comprising the steps of: filling a syringe with a local anesthetic; administering said anesthetic to a biopsy site of a patient; removing a needle from the end of said syringe to expose a biopsy punch mounted on the end of said syringe; excising a specimen of skin with a sharpened end of said punch from said biopsy site; extracting said specimen from said biopsy punch by depressing a plunger of said syringe; retracting said plunger to space the end of said plunger from the end of said sharpened end of said punch; cutting a cylindrical portion of an open cell surgical sponge with said biopsy punch; and implanting said cylindrical portion of said open cell sponge into a wound caused by said excising of said specimen.

10. A method for conducting a skin biopsy procedure, comprising the steps of: filling a syringe with a local anesthetic; administering said anesthetic to a biopsy site of a patient; removing a needle from the end of said syringe to expose a biopsy punch mounted on the end of said syringe; rotating said plunger of said syringe to increase the maximum travel of said plunger; excising a specimen of skin with a sharpened end of said punch from said biopsy site; extracting said specimen from said biopsy punch by depressing a plunger of said syringe; implanting said cylindrical open cell sponge portion into a wound caused by said excising of said specimen.

11. The method recited in claim 10 further comprising the step of applying pressure to said sponge for 30 to 60 seconds.

12. The method recited in claim 10 further comprising the step of cleaning and draping said biopsy area before the excising of said specimen.

* * * * *